United States Patent [19]

Chapman et al.

[11] 4,144,281
[45] Mar. 13, 1979

[54] HF ALKYLATION PROCESS UTILIZING COMPRESSED ISOPARAFFIN VAPOR IN INDIRECT HEAT EXCHANGES

[75] Inventors: Charles C. Chapman; Paul D. Hann, both of Bartlesville, Okla.

[73] Assignee: Phillips Petroleum Company, Bartlesville, Okla.

[21] Appl. No.: 900,554

[22] Filed: Apr. 27, 1978

[51] Int. Cl.² ............................................. C07C 3/54
[52] U.S. Cl. ............................................. 260/683.48
[58] Field of Search ...................... 260/683.48, 683.43

[56] References Cited

U.S. PATENT DOCUMENTS

| | | | |
|---|---|---|---|
| 2,431,500 | 11/1947 | Penick | 260/683.48 |
| 2,764,623 | 9/1956 | Leonard et al. | 260/683.48 |
| 3,002,818 | 10/1961 | Berger | 260/683.48 |
| 3,594,444 | 7/1971 | Jones | 260/683.48 |
| 3,857,904 | 12/1974 | Chapman | 260/683.48 |
| 3,957,901 | 5/1976 | Chapman | 260/683.43 |

Primary Examiner—George Crasanakis

[57] ABSTRACT

In an HF alkylation of an isoparaffin, e.g., isobutane, with olefins, the hydrocarbon phase from the HF reactor effluent settler is charged to an HF separation zone. HF-free bottoms from the HF separation zone are charged to an isobutane stripper thereby producing HF-free isobutane vapor as overhead. The heat available in the isobutane vapor overhead is then utilized by compressing the vapor and using it as additional heat exchange fluid prior to being recycled to the HF alkylation. The compressed vapor can, for example, be used to reboil the HF separation zone, e.g., an HF stripper, heat the inner-heater on the isobutane stripper, and heat the depropanizer inner heater.

8 Claims, 2 Drawing Figures

HF ALKYLATION PROCESS UTILIZING COMPRESSED ISOPARAFFIN VAPOR IN INDIRECT HEAT EXCHANGES

BACKGROUND OF THE INVENTION

This invention relates to a process for the production of higher boiling hydrocarbons from lower boiling hydrocarbons in the presence of catalytic agents. Another aspect of the present invention relates to a process for the alkylation of isoparaffins such as isobutane with olefins in the presence of a hydrofluoric acid catalyst. Another aspect of this invention relates to the processing of HF alkylation hydrocarbon effluent initially with HF stripping so that subsequently recovered isobutane stripper overhead vapors will be HF-free and can then be compressed and used as additional heat exchange fluid prior to being recycled to the HF alkylation. This invention also relates to the use of HF-free, compressed isobutane stripper overhead vapors to reboil an HF separation zone such as an HF stripper. In another aspect, this invention relates to an alkylation process wherein compressed HF-free isobutane stripper overhead vapors are used to (1) reboil the HF stripper, (2) heat the inner heater on the isobutane stripper and (3) heat the depropanizer inner heater.

As is well known, hydrocarbon products may be produced by alkylation reactions involving the combination or condensation of two dissimilar hydrocarbon reactants in the presence of suitable catalytic agents. While various types of alkylate products may be obtained by employing various types of reactants, the alkylation of low boiling isoparaffins, such as isobutane and isopentane, with low boiling olefins, such as ethylene, propylene, the isomeric butenes, and the isomeric pentenes, for the production of various fuels has become of particular importance. Liquid hydrogen fluoride (hydrofluoric acid) has found favor as a catalyst in this type of reaction.

The alkylation of isobutane with olefins is representative of this type of reaction and has been commonly carried out by feeding isobutane and olefin feed stocks in the liquid state along with hydrofluoric acid to an alkylation reactor such as a riser reactor. The reaction product stream is then passed to various separation zones such as an HF stripper, an isobutane stripper and a propane stripper in order to recover the various components of the stream. The energy requirements for heating the various separation zones and streams are great and it would be desirable, due to the high cost of energy, to use an energy conserving alkylation process.

It is an object of this invention, therefore, to provide an improved alkylation process.

Another object of this invention is to utilize the available heat in an HF alkylation plant in a more efficient manner.

It is another object of this invention to cut down on the energy costs of an alkylation process.

Other aspects, objects, and advantages of the present invention will become apparent from a study of the disclosure, the appended claims, and the drawings.

SUMMARY OF THE INVENTION

In accordance with the invention, the above objects are achieved by a process wherein the isoparaffin stripper overhead vapor stream is compressed and used as additional heat exchange fluid prior to being recycled to the HF alkylation reaction zone. The isoparaffin, olefin and hydrofluoric acid catalysts are reacted in a reaction zone such as a riser reactor to form an alkylate. Upon the separation of the hydrofluoric acid from the hydrocarbon constituents of the reaction mixture to yield a substantially hydrofluoric acid free hydrocarbon stream, the hydrocarbon stream is introduced into an isoparaffin stripping zone, which is HF-free isoparaffin stripper and the propane stripper (depropanizer). The compressed isoparaffin vapor can also be used in an indirect heat exchange relationship with feed streams to various separation zones such as the feed to the HF stripper.

After the isoparaffin vapor is used in its heat exchange fluid capacity, the isoparaffin is then recycled to the HF alkylation reaction zone. The isoparaffin to which this invention is most applicable is that of isobutane.

DETAILED DESCRIPTION OF THE INVENTION

Figure 1:
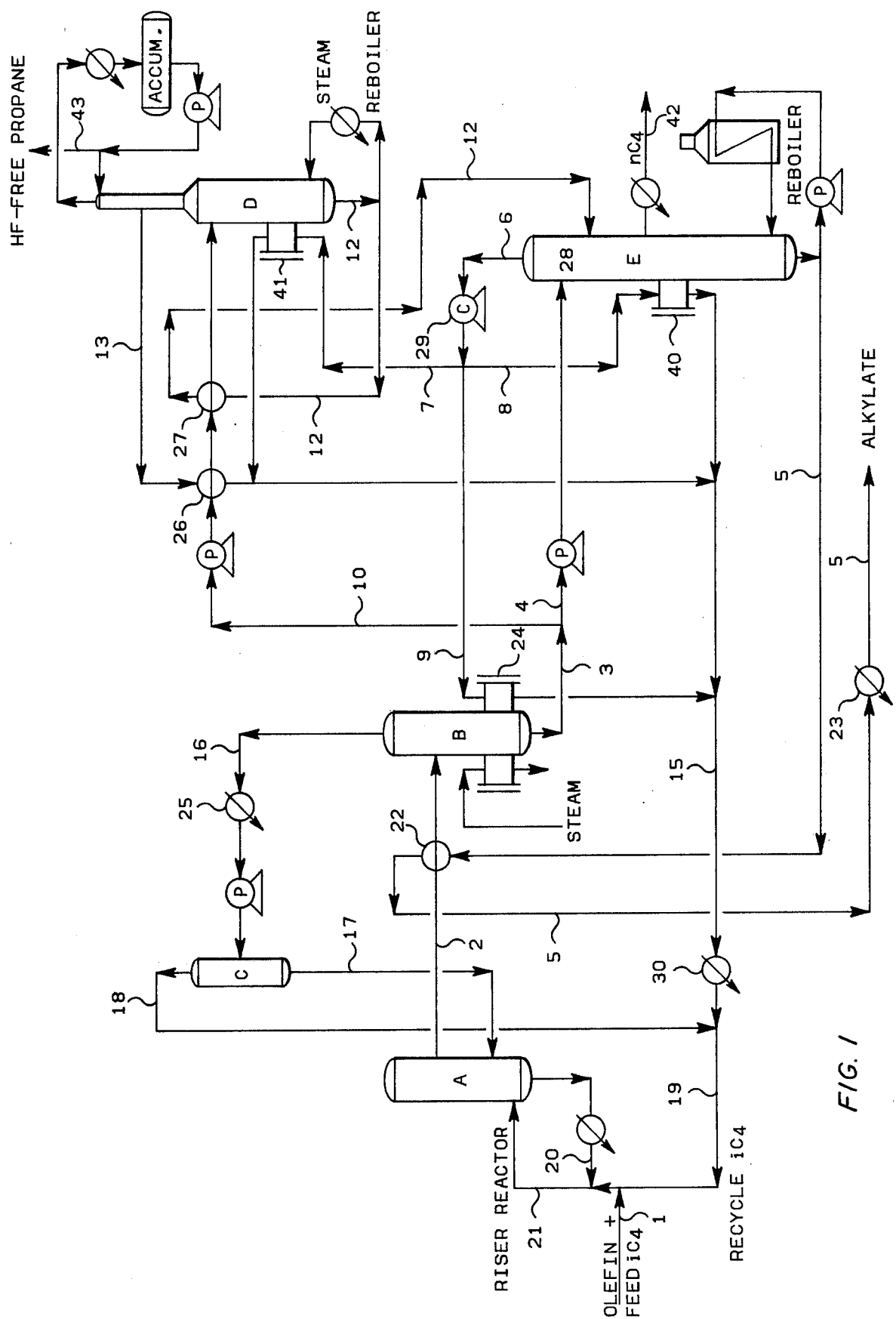
FIG. 1 is a schematic of an embodiment of the present invention in which HF-free isobutane vapor is split into three streams. One stream is used to reboil the HF acid stripper, another stream is used to heat the innerheater of the isobutane stripper, and the third stream is used to heat the inner heater of the depropanizer.

This invention relates to an alkylation process in which energy is used efficiently and effectively, thereby cutting down on high energy costs, through the use of the heat of vaporization of HF-free isoparaffin vapor. The isoparaffin vapor is used in a number of indirect heat exchanges. The importance and desirability of this invention increases as the cost of energy increases and the need for conservation of energy continues.

The process of this invention comprises a reaction of an isoparaffin, of which isobutane is the most preferred and in which context this invention will be described, and olefins such as propylene and/or the butylenes, isobutylene, butene-1, cis- and trans-butene-2, in the presence of hydrofluoric acid in an HF alkylation reaction zone. The type of reaction zone is not of significant importance and one that is commonly used for this type of reaction is a riser reactor. The reaction mixture is then passed to an acid settler from which the liquid hydrocarbon phase thereof is passed to an HF separation zone, e.g. HF stripper. The particular type of HF separation zone is not important as long as the separation zone removes substantially all of the hydrofluoric acid to yield a substantially HF-free hydrocarbon stream.

A substantially HF-free hydrocarbon stream is then split into two streams with one stream sent to a propane stripper or depropanizer in an amount to rid the system of charged propane and produced propane, and the other stream sent to an isobutane stripper (isostripper).

Several advantages of the process of this invention are herein apparent in that since the charge to the depropanizer is HF-free, the depropanizer can be operated at a lower pressure than in conventional alkylation processes. The pressures employed can be advantageously about 90 psi lower than conventional pressures.

The fact that the charge to the isobutane stripper or isostripper is HF-free results in a substantially HF-free isobutane vapor overhead which can then be safely compressed in a conventional compressor with no danger of corrosion. Due to the low concentration or trace of HF, the isobutane vapor can be compressed by conventional equipment and therefore will result in a definite economic advantage in compressor design. It is the low concentration of HF in the isobutane vapor which allows the vapor to be compressed economically and thereby allow the sensible heat and the contained heat of vaporization of the substantially HF-free isobutane vapor to be utilized effectively as the compressed isobutane vapor can then be used as a heat exchange fluid before being recycled as liquid to the alkylation reaction zone. Compressed vapor can be placed in indirect heat exchange relationship with the HF stripper, the depropanizer, the isostripper, and even the feed stream to the HF stripper. Through the use of the compressed isobutane vapor in areas of heating which would normally use an independently heated heat exchange fluid, energy savings are realized in the alkylation process of the present invention.

Further details of this invention will become apparent from the following detailed description of the drawings and the examples. The following embodiments are not intended to limit the invention in any way and are given only for illustration. Although the descriptions are given in terms of isobutane, the invention is applicable to any appropriate isoparaffin.

Referring now to FIG. 1 of the drawings, olefins and isobutane feed (1) along with recycle isobutane (19) are contacted with cooled recycle HF catalyst (20) and is charged to HF alkylation reaction zone (21). The hydrocarbon phase (2) from the phase separation (reactor settler) A is preheated indirectly at (22) by isostripper bottoms (5) and charged to the HF stripper B. The isostripper bottoms (5) is then cooled by heat exchange (23) and then taken away for storage or further use.

HF stripper B is reboiled indirectly at (24) by a portion of the compressed, HF-free isobutane stripper overhead vapors (9). The HF stripper overhead (16) is cooled and condensed (25) and pumped to a liquid-liquid separator C. Recovered acid phase is then returned via (17) to the reactor settler A. The hydrocarbon phase (18) is then recycled via (19) to the alkylation zone.

The HF stripper bottoms (3) is divided into two streams with one stream (10) to remove charged and produced propane being pumped before indirect heating at (26) and (27) with the liquid isobutane-rich side-draw (13) and with the reboiled bottoms (12) from the depropanizer D. The bottoms (12) from the depropanizer D, which contains alkylate, is then charged to isostripper or the deisobutanizer E at (28). The second portion (4) of the HF stripper bottoms (3) is pumped into the top locus of the isobutane stripper E. Bottoms (5) of isobutane stripper E is used in an indirect heat exchange relationship at (22). HF-free, hot isobutane vapor overhead (6) is compressed at (29) and split into three streams, (7), (8) and (9). Stream (9) is used to indirectly reboil HF stripper B at (24). The isobutane vapor of stream (9) is then recycled to the alkylation reaction zone via (15), cooler (30), and conduit (19).

Stream (8) is used to indirectly heat the inner heater (40) on the isostripper and is then recycled to the alkylation reaction zone via (15), cooler (30), and conduit (19).

Stream (7) is used to indirectly heat the inner heater (41) on the depropanizer D and is then combined with the liquid isobutane-rich side-draw stream (13). The combined stream is then recycled to the alkylation reaction zone via (15), cooler (30), and conduit (19).

Normal butane vapor is removed from isostripper E, condensed, and recovered at (42). HF-free propane is recovered at (43).

Figure 2:
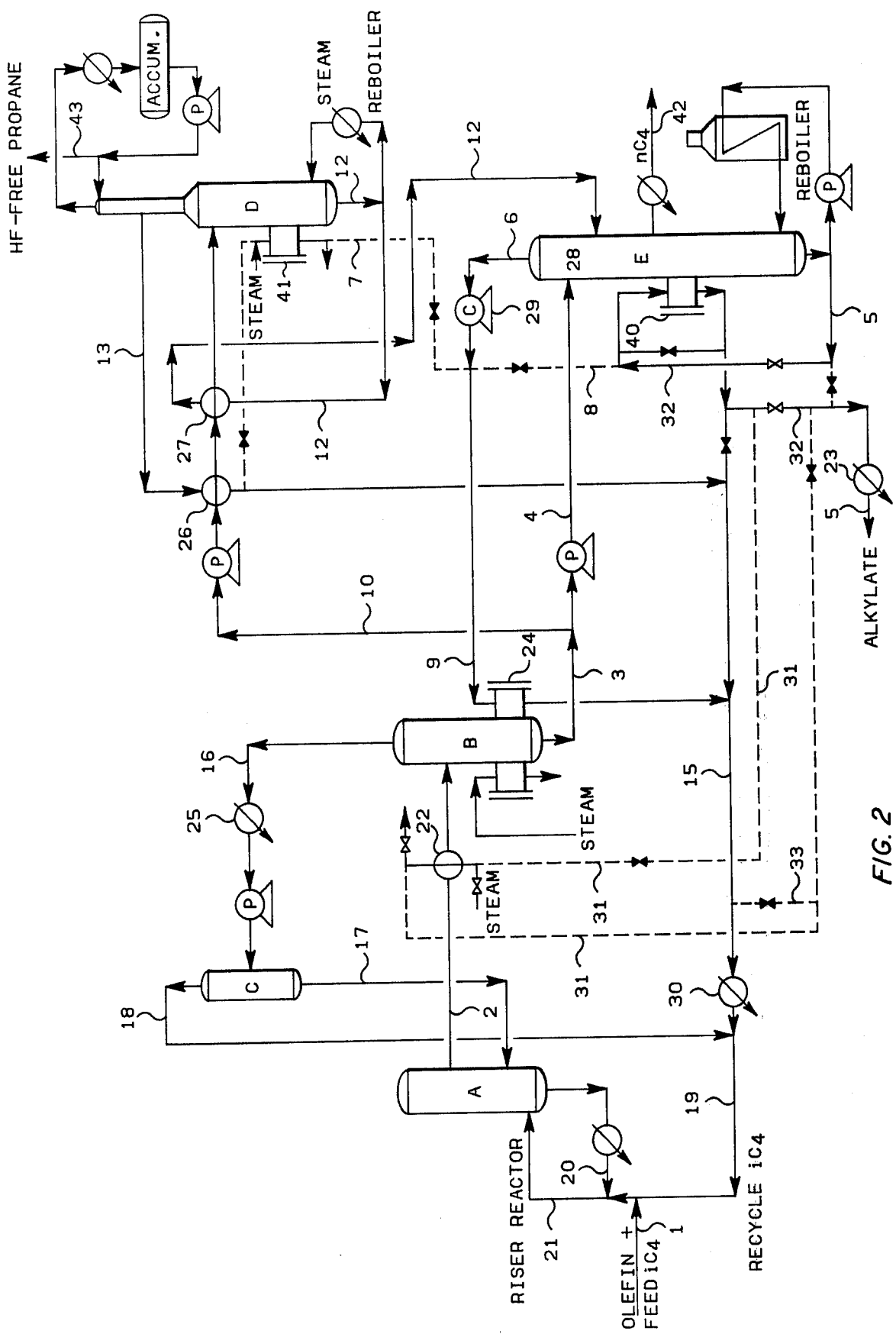
FIG. 2 shows an embodiment of the present invention where isobutane compressed vapor is used primarily to reboil the HF acid stripper. Optionally, the compressed isobutane vapor can be used to heat the innerheater of the isobutane and propane strippers as well as the feed stream to the HF acid stripper.

Referring now to FIG. 2, a diagrammatic view of a system for producing an alkylate product stream is shown wherein the HF-free overhead isobutane vapors (6) from the isostripper E are compressed at (29) and used solely to reboil the HF stripper B at (24). The isobutane overhead is then recycled to the alkylation reaction zone (21) via (9), (15), cooler (30), and conduit (19). The bottoms (5) from isostripper E is passed via (32) to heat inner heater (40). Steam is used to preheat stream (2) in (22), and steam is used to inner heater (41). The remaining elements are the same as in the system shown in FIG. 1.

A calculated example of the process of this invention carried out in a system as shown in FIG. 2 is as follows. Vessel conditions, as well as stream compositions and quantities (moles per hour), are set out.

CALCULATED EXAMPLE

Operating Conditions:

Vessel (E) Isostripper (55 Trays):
| | |
|---|---|
| Pressure, psia., | |
| Top, | 100 |
| Bottom, | 105 |
| Temperature, °F., | |
| Top, | 135 |
| Bottom, | 325 |
| Reboiler Duty, Btu/hr., | 81,000,000 |

Vessel (D) Depropanizer (50 Trays):
| | |
|---|---|
| Pressure, psia., | |
| Top, | 245 |
| Bottom, | 249 |
| Temperature, °F., | |
| Top, | 121 |
| Bottom, | 242 |
| Reboiler Duty, Btu/hr., | 56,000,000 |
| Condenser Duty, Btu/hr., | 44,300,000 |

Vessel (B) HF Acid Stripper (25 Trays):
| | |
|---|---|
| Pressure, psia., | |
| Top, | 150 |
| Bottom, | 157 |
| Temperature, °F., | |
| Top, | 144 |
| Bottom, | 166 |
| Reboiler Duty, Btu/hr., | 75,800,000 |
| Condenser Duty, Btu/hr., | 45,700,000 |

HF Alkylation and Settler (A) Unit:
| | |
|---|---|
| Pressure, psia., | 160 |
| Temperature, °F., | 90 |
| Total Isobutane/Olefin Mol Ratio, | 12 |
| HF/Total Hydrocarbon, vol., ratio | 4:1 |

Stream Compositions and Quantities (Mols/hr.)

| Components | (2) | (3) | (4) | (5) | (6) | (9) | (10) | (12) | (13) | (43) | (15) | (16) | (17) | (18) | (19) |
|---|---|---|---|---|---|---|---|---|---|---|---|---|---|---|---|
| HF | 697 | (a) | (b) | — | (b) | (b) | (b) | — | — | (b) | (b) | 697 | 532 | 165 | 165 |
| Propane | 1,600 | 800 | 400 | — | 400 | 400 | 400 | — | 200 | 200 | 600 | 800 | 3 | 797 | 1,397 |
| Isobutane | 17,625 | 13,834 | 6,917 | 2 | 8,634 | 8,634 | 6,917 | 1,729 | 5,185 | 3 | 13,819 | 3,791 | 7 | 3,784 | 17,603 |
| Normal Butane | 1,915 | 1,670 | 835 | 98 | 939 | 939 | 835 | 342 | 493 | — | 1,432 | 245 | — | 245 | 1,677 |
| IC$_5$ Plus | 1,933 | 1,900 | 950 | 1,730 | 112 | 112 | 950 | 903 | 47 | — | 159 | 33 | — | 33 | 192 |

-continued

| Components | Stream Compositions and Quantities (Mols/hr.) | | | | | | | | | | | | | | |
|---|---|---|---|---|---|---|---|---|---|---|---|---|---|---|---|
| | (2) | (3) | (4) | (5) | (6) | (9) | (10) | (12) | (13) | (43) | (15) | (16) | (17) | (18) | (19) |
| Total | 23,770 | 18,204 | 9,102 | 1,830 | 10,085 | 10,085 | 9,102 | 2,974 | 5,925 | 203 | 16,010 | 5,566 | 542 | 5,024 | 21,034 |
| Temperature, °F., | 118 | 160 | 160 | 325 | 135 | 206 | 180 | 242 | 196 | 121 | 202 | 144 | 100 | 100 | 90 |
| Pressure, psia., | — | — | — | — | 100 | 250 | — | — | — | — | — | — | — | — | — |

Notes:
(a) = 0.24 × 10$^{-11}$ Mol/hr. HF
(b) = 0.12 × 10$^{-11}$ Mol/hr. HF

The total utilities gain to the use of the process of the present invention is estimated at approximately $3,229 per day. The overhead vapors (6), which are substantially HF-free and can be safely compressed in a conventional compressor with no danger of corrosion, are at 100 psia and 135° F. before compression. The overhead vapors are then compressed to 250 psia and are at 206° F. after compression. The compressed stream is referred to as stream (9) in FIG. 2. Stream (9) then indirectly heats the heat exchanger (24) of the HF stripper B, after which the used vapors are at 240 psia and 175° F. This amounts to 73,000,000 Btu/hr. for heating. If one approximates the cost of heat at $2.50 per million Btu's, the value of this heat is $4,380/day. Compression costs, however, are $1,247 per day if one estimates at 3,150 kilowatts per hour are used by the compresser and the cost of a kilowatt is $1.65. By using compression, various pumping costs are decreased, e.g. on recycled isobutane (15) charged to the alkylation reaction zone, which amount to 244 kilowatts per hour or $96/day. The total utilities gain by the invention, therefore, is $3,229/day. With the cost of natural gas approximated at $2.50 per 1,000 standard cubic feet and 1,000,000 Btu's are obtained for every 1,000 standard cubic feet of natural gas, this is an equivalent savings of 1,290,000 standard cubic feet of natural gas per day.

FIG. 2 further depicts another embodiment of the present invention in which the compressed overhead isobutane vapor is not only used to reboil the HF stripper B, but is also used to heat the innerheater (41), of the depropanizer D and innerheater (49) of the isobutane stripper E as well as to heat the stream (2) charged to the HF stripper B. This embodiment is depicted by the dashed lines.

The overhead isobutane vapor (6) from the isostripper E is compressed at (29) and split into three separate streams. The first stream (7) is used to heat the innerheater (41) of the depropanizer D and is then combined with stream (13) to be recycled to the alkylation reaction zone (21) via conduit (15), cooler (30), and conduit (19).

Stream 8 is used to heat the innerheater (40) on the isobutane stripper E and then via (31) to heat the stream 2 to be charged to the HF stripper B at (22). The used isobutane vapor of stream, now numbered (33), to conduit (15) from which it is recycled to the alkylation reaction zone (21).

Stream 9 is used to reboil the HF stripper B at (24) and then recycled to the alkylation reaction zone as disclosed previously.

Also bottoms stream (5) can be used to first heat innerheater (40) and then to preheat stream (2) at (22). The flow is from (5), (32), innerheater (40), (31), exchanger (22), (31) and exchanger (32), and conduit (5).

Reasonable variations and modifications are possible within the scope of the foregoing disclosure and the appended claims to the invention.

We claim:

1. An alkylation process which comprises the steps of:
    contacting an olefin and isoparaffin with an HF acid catalyst under alkylation conditions to form an alkylation reaction effluent comprising alkylate, isoparaffin, HF acid, and non-reacted paraffins,
    passing said reaction effluent to a phase separation zone and allowing said effluent to separate into a hydrocarbon phase and an acid phase,
    passing said hydrocarbon phase to an HF acid stripping zone and therein subjecting said hydrocarbon phase to such stripping conditions as to remove overhead an HF acid phase and as bottoms a hydrocarbon phase substantially free of HF,
    passing said bottoms hydrocarbon phase removed from said HF acid stripping zone to an isoparaffin stripping zone and removing overhead therefrom an isoparaffin vapor stream substantially free of HF,
    compressing said overhead isoparaffin vapor stream,
    passing said compressed isoparaffin vapor stream in indirect heat exchange relationship with a lower portion of said HF acid stripping zone as a source of heat for said removal of HF acid phase from the hydrocarbon phase, and
    withdrawing said alkylate from said isoparaffin stripping zone.

2. A process in accordance with claim 1 wherein the isoparaffin vapor stream is recycled to the alkylation reaction step after said indirect heat exchange relationship.

3. A process in accordance with claim 1 wherein said isoparaffin is isobutane.

4. A process in accordance with claim 3 wherein a portion of said hydrocarbon phase from said HF stripping zone is introduced into a propane stripping zone,
    the compressed overhead isobutane vapor stream is split into three streams wherein
    a first stream of said isobutane vapor is passed into indirect heat exchange relationship with said lower portion of said HF acid stripping zone,
    a second stream of said isobutane vapor is passed into indirect heat exchange relationship with an innerheater of the isobutane stripping zone and
    a third stream of said isobutane vapor is passed into indirect heat exchange relationship with an innerheater of the propane stripping zone.

5. A process in accordance with claim 4 wherein said three streams are recycled to the alkylation reaction step after each of said indirect heat exchange relationship.

6. A process in accordance with claim 4 wherein said stream passed into indirect heat exchange relationship with the innerheater of said isobutane stripping zone is then passed into indirect heat exchange relationship with said hydrocarbon phase being passed to said HF acid stripping zone.

7. A process for forming an alkylate product comprising the steps of:
   (a) reacting an olefin and isobutane in the presence of hydrofluoric acid alkylation catalyst to form an alkylate product stream,
   (b) passing said alkylate product stream from step (a) to a phase separation zone to separate said product stream into a first hydrocarbon phase and an acid phase,
   (c) passing said hydrocarbon phase from step (b) to an HF acid stripping zone to separate a substantially HF-free hydrocarbon phase as a bottoms stream from an overhead HF-containing vapor stream,
   (d) condensing the vapor stream from step (c) into an HF phase and a second hydrocarbon phase,
   (e) separating the condensed HF phase from said second hydrocarbon phase,
   (f) returning the HF phase from step (e) to the phase separation zone of step (b) and returning the second hydrocarbon phase from step (e) to the alkylation reaction of step (a),
   (g) charging a first portion of said substantially HF-free hydrocarbon phase from step (c) to an isobutane stripper and a second portion of said hydrocarbon phase from step (c) to a depropanizing zone,
   (h) separating an isobutane vapor and an alkylate product stream from said isobutane stripper,
   (i) compressing said isobutane vapor from step (h) and passing a first portion of said compressed vapor in indirect heat exchange relationship to reboil said HF acid stripping zone, passing a second portion of said compressed vapor in indirect heat exchange relationship with an innerheater in said isobutane stripper and passing a third portion of said compressed vapor in indirect heat exchange relationship with an innerheater in said depropanizing zone,
   (j) recycling the three portions of said isobutane vapor after being used in said indirect heat exchange relationship in step (i) to the alkylation reaction of step (a).

8. A process in accordance with claim 7 further comprising the steps of
   (k) withdrawing a liquid isobutane side-draw from the depropanizing zone and passing said liquid side-draw in indirect heat exchange relationship with the feed stream to the depropanizing zone,
   (l) passing the bottoms of the depropanizing zone in indirect heating exchange relationship with the feed to the depropanizing zone and then charging said bottoms to an intermediate locus in the isobutane stripper, and
   (m) passing the isobutane stripping zone bottoms in indirect heat exchange relationship with the hydrocarbon phase being passed to the HF acid stripping zone in step (c).

* * * * *